United States Patent [19]

Prillieux et al.

[11] 4,172,844

[45] Oct. 30, 1979

[54] ALKYLARYL SULPHONIC ACIDS

[75] Inventors: Marcel Prillieux; Marcel Robert; Robert Tirtiaux, all of Mont-Saint-Aignan, France

[73] Assignee: Exxon Research & Engineering Co., Florham Park, N.J.

[21] Appl. No.: 557,396

[22] Filed: Mar. 11, 1975

[30] Foreign Application Priority Data

Mar. 13, 1974 [FR] France .............................. 74 08432

[51] Int. Cl.² .......................................... C07C 143/24
[52] U.S. Cl. ................................................ 260/505 P
[58] Field of Search ..................................... 260/505 P

[56] References Cited

U.S. PATENT DOCUMENTS

| | | | |
|---|---|---|---|
| 2,373,793 | 4/1945 | Susie | 260/505 P |
| 2,500,024 | 3/1950 | Cornell et al. | 260/505 |
| 2,522,518 | 9/1950 | Kleinholz et al. | 260/505 |
| 2,652,427 | 9/1953 | Schultz | 260/505 |
| 2,706,736 | 4/1955 | Birch et al. | 260/505 |
| 3,681,443 | 8/1972 | Benson et al. | 260/505 |

FOREIGN PATENT DOCUMENTS 849183 9/1960 United Kingdom.
1258249 10/1968 United Kingdom.
1306226 1/1969 United Kingdom.

*Primary Examiner*—A. Siegel
*Attorney, Agent, or Firm*—Frank T. Johmann

[57] ABSTRACT

The development of color of a concentrate of alkarylsulphonic acids is reduced by adding to and dissolving in the freshly prepared concentrate up to 5% of its weight of an organic compound having at least one ether group therein, the partial vapor pressure of the compound thus dissolved in the concentrate being negligible at the temperatures at which the concentrate is stored or transported. Examples of suitable organic compounds are aliphatic or phenolic monoethers, e.g. diethylene glycol.

12 Claims, No Drawings

ALKYLARYL SULPHONIC ACIDS

The invention is concerned with alkarylsulphonic acid. These acids and their salts are surface-active products which are employed in various industries; those which are soluble in hydrocarbon oils are used for making lubricating products. The invention relates to a process for reducing colour development in alkarylsulphonic acids. It also covers the concentrates whose colour is stabilised by means of this process.

The invention relates to alkarylsulphonic acids which are soluble in water, and to those which are soluble in hydrocarbon oils.

The former are obtained by sulphonation of hydrocarbons belonging to the lower members of the aromatic series. These hydrocarbons include in particular benzene, toluene and those of their homologues whose molecule contains up to 19 carbon atoms. They also include in particular naphthalene, methylnaphthalenes and those of their homologues whose molecule contains up to 19 carbon atoms.

The invention is concerned more especially with alkarylsulphonic acids that are soluble in hydrocarbon oils. These acids are obtained by sulphonation either of mineral oils, or of hydrocarbons that belong to the higher terms of the aromatic series and are prepared by synthesis. This synthesis comprises alkylating benzene, toluene, xylenes, naphthalene etc, with chloroparaffins or olefins the molecule of which usually contains at least 9 carbon atoms.

The sulphonation of aromatic hydrocarbons is a well-known operation. It can be carried out in particular by means of sulphur trioxide dissolved in liquid sulphur dioxide, at low temperature.

As a rule, the mean molecular weight of the alkarylsulphonic acids that are soluble in hydrocarbon oils is above 350. Alkarylsulphonic acids whose molecular weight is of the order of 600, and even heavier acids are manufactured on an industrial scale. The more usual of these acids have a mean molecular weight of between 400 and 550.

In the pure state, the alkarylsulphonic acids are too viscous for it to be possible to transport and use them at moderate temperatures. They must therefore be thinned with a hydrocarbon oil on manufacture. A concentrate is thus obtained which contains from 50 to 90%, or more usually from 70 to 90% of its weight of alkarylsulphonic acids. Nevertheless this concentrate is still too viscous for it to be possible to pump it at the ordinary temperature; it is frequently necessary to maintain it at temperatures from 60° to 120° C. in the tanks where it is stored.

Now alkarylsulphonic acids are rather unstable products. Although it is very slow, their decomposition is definitely detectable at temperatures above 60° C. This degradation above all manifests itself in the development of the colour of the concentrate. By neutralising with a base, usually sodium hydroxide or lime, a concentrate in which only 1 to 2% of the alkarylsulphonic acids have decomposed, the sulphonate obtained has an undesirable composition.

The present invention aims at proposing means for lessening the colour development of the concentrates of alkarylsulphonic acids.

The applicants have discovered that a small proportion of an ether, added to a concentrate of already prepared alkarylsulphonic acids had the unexpected effect of limiting the colour development of this product.

According to this invention development of colour is at least minimised by a process which comprises adding and dissolving in the freshly prepared concentrate of alkarylsulphonic acid a small quantity of an organic compound which contains at least one ether group therein.

The partial vapour pressure of the compound thus dissolved in the concentrate should be negligible at the temperatures at which the concentrate is stored or transported. As a rule, a compound having a boiling point exceeding 100° C., or better still, 120° C., meets this condition.

This organic compound can contain, in addition to the ether group, other functional groups. Preferably, use is made of a compound having at the same time at least one ether group and one or more alcohol groups.

Thus, one can use ethers of the formula R—o—R' where R and R' are hydrocarbyl groups. R' and R' can be branched or straight chain alkyl, aryl, alkaryl or aralkyl and contain for example 1 to 20 carbon atoms, e.g. 4–10 carbon atoms. In particular, the ethers that can be used comprise aliphatic monoethers of rather high boiling point, in particular those whose molecule contains from 7 to 8 carbon atoms, such as di n-butyl ether. it is also possible to use a phenolic monoether, such as anisole (methoxybenzene), phenetol (ethoxybenzene), diphenyl ether etc. Mention may also be made, for instance, of dibenzyl ether. Phenolic ethers are to be preferred.

Suitable ether alcohols include those of the formula R"—(O—(CH$_2$)$_x$)$_n$—OH where R" is a hydrocarbyl group, x is an integer, preferably 2 or 3, and n is an integer preferably 1 to 10. R" may be branched or straight chain alkyl; and alkaryl or aralkyl and contains for example 1 to 20, e.g. 2 to 6 carbon atoms. Thus the ether alcohols that can be used include in particular the monoethers of ethylene glycol or propylene glycol, in particular monomethyl ethers, monoethyl or monobutyl ethers of ethylene glycol. They also include diethylene glycol, dipropylene glycol as well as the monoethers of these diglycols, in particular monomethyl or monoethyl ethers of these diglycols.

It is likewise possible to use the polyalkylene glycols that are soluble in the concentrates under consideration, in particular the polycondensates of ethylene oxide and propylene oxide and the monoethers of these polyalkylene glycols.

It has been noted that anisole, monoethyl ether of ethylene glycol (cellosolve), ethylene glycol monomethylether and diethylene glycol monoethyl ether (carbitol) are particularly efficacious.

It is possible to add without trouble to the already prepared concentrate of alkaryl sulphonic acids up to 5% of the weight (e.g. 0.05 to 5%) of the compound with ether group. It is generally sufficient to add 0.2 to 1%. A smaller proportion may be added, for instance between 0.05 and 0.2%, but the effect obtained is less marked.

The invention does not only relate to the process which has just been described, but also to the concentrate the colour of which is stabilised by means of this process.

This concentrate of alkarylsulphonic acids according to the invention contains up to 5% by weight, e.g. from 0.05 to 5%, or for preference from 0.2 to 1% of its weight of the compound specified above.

The invention relates more particularly to a concentrate containing from 50 to 90% of its weight of alkarylsulphonic acids that are soluble in hydrocarbon oils, these acids being diluted with an oil of this type. This concentrate is characterised in that it moreover contains, according to the invention, from 0.05 to 5%, or for preference from 0.2 to 1% of its weight of the compound specified above.

The following Example is given to illustrate the present specification. It is not restrictive and the scope of the invention is not restricted by the particular features that are peculiar to it.

EXAMPLE

This example relates to tests that have been carried out on samples of a concentrate of alkylbenzene sulphonic acids.

The concentrate to which these tests related is an industrial product which is in regular production. It contains 90% by weight of sulphonic acids and 10% oil.

These sulphonic acids are obtained by sulphonation by means of $SO_3$ dissolved in liquid $SO_2$ of monoalkylbenzenes resulting from the alkylation of benzene with propylene oligomers. The mean no. of carbon atoms of these oligomers is about 24 atoms per molecule.

The mean molecular weight of these sulphonic acids is about 500.

The oil present in the concentrate consists of the hydrocarbons of the alkylate which have not been sulphonated. It contains saturated hydrocarbons and alkylbenzenes. Its viscosity is about 20 cSt at 60° C.

This concentrate of alkylbenzene sulphonic acids is a very viscous liquid. Its viscosity is:

1300 cSt at 60° C.
650 cSt at 70° C.
350 cSt at 80° C.

It is commonly admitted that it is difficult to pump a liquid whose viscosity exceeds 350 cSt. This concentrate must therefore be maintained at temperatures exceeding 80° C. in the storage tanks. Owing to the viscosity of the product, the latter is heated locally to higher temperatures which sometimes reach 120° C.

A certain quantity of the concentrate which had just been made was removed. A sample of this freshly made concentrate was at once neutralised so as to obtain a concentrate of sodium sulphonates. The sample of sulphonates thus prepared was kept as a control.

Sample of the concentrate of sulphonic acids as such and samples of the same concentrate with the addition of 0.5% of its weight of a stabiliser were kept at 80° C. for two months. Another set of samples was maintained at 120° C. for 60 hours.

The samples thus tested were next neutralised with sodium hydroxide, so as to obtain the corresponding sodium sulphonate concentrates. Finally, the colouration of these sulphonates was assessed.

To assess the colouration of a concentrate of sulphonates, the latter are diluted with white spirit so as to prepare a solution containing 7% by weight of pure sulphonates. The colouration of the solution thus obtained was evaluated in accordance with French standard NFT 60-104 (this standard corresponds to American standard ASTM D-1500).

The results obtained are collated in the following table:

| Stabiliser added to sulphonic acid concentrate | Colouration of sulphonates corresponding to acids tested: | |
|---|---|---|
| | 2 months 80° C. | 60h. 120° C. |
| None | 4.5 | 6 |
| Diethylene glycol | 4.0 | 4.5 |
| Cellosolve (monoethylether of ethylene glycol) | 3.0 | 4.05 |
| Butylcellosolve (monobutylethyl of ethylene glycol) | 4.0 | 4.5 |
| Polyalkylene glycol (polycondensate of 30% ethylene oxide and 70% propylene oxide) | 4.0 | 4.5 |
| Methylcellosolve (monomethylether of ethylene glycol) | 3.0 | 4.5 |
| Carbitol (monoethylether of diethylenw glycol) | 3.0 | 4.0 |
| Butylcarbitol (monobutylether of diethylene glycol) | 4 | 4.5 |
| Anisole (methoxybenzene) | 4 | 3.5 |
| Diphenyl ether | 4 | 4.5 |

What is claimed is:

1. A process for reducing the development of color due to degradation of a concentrate comprising 50 to 90 wt. % of oil soluble alkarylsulphonic acid having a mean molecular weight of about 350 to about 600, said acid having been prepared by sulfonation with $SO_3$ dissolved in liquid $SO_2$; and a hydrocarbon oil as diluent; said process comprising adding to and dissolving in said concentrate, a degradation inhibiting amount, in the range of about 0.05 up to 5% by weight, based on the weight of said concentrate, of an organic compound selected from the group consisting of:

(a) ether of the formula:

ROR' wherein R and R' are each hydrocarbyl groups of 4 to 10 carbon atoms;

(b) ether alcohol of the formula:

R"—(O—(CH$_2$)$_x$)$_n$—OH wherein R" is an alkyl group of 2 to 6 carbon atoms, x is 2 to 3, and n is 1 to 10;

(c) polyalkylene glycol of ethylene oxide and/or propylene oxide; and (d) phenolic monoether selected from the group consisting of methoxybenzene and ethoxybenzene.

2. A process according to claim 1, in which the boiling point of said organic compound exceeds 120° C.

3. A process according to claim 1 in which said organic compound is said ether of group (a).

4. A process according to claim 1 wherein the organic compound is the ether alcohol of group (b) wherein R" is alkyl of 2 to 6 carbon atoms.

5. A process according to claim 1 in which said organic compound is said polyalkylene glycol of group (c).

6. A process according to claim 1 in which said organic compound is said phenolic monoether of group (d).

7. A process for reducing the development of colour due to degradation of a concentrate comprising 50 to 90 wt. % of oil soluble alkarylsulphonic acid having a mean molecular weight of about 350 to 600, and a hydrocarbon oil as diluent; which comprises adding to said concentrate, and after the formation and purification of said acid has been completed, a degradation inhibiting amount, in the range of about 0.05 up to 5 wt. %, based on the weight of said concentrate, of an organic compound selected from the group consisting of:

(a) ether of the formula:

ROR"

wherein R and R' are each hydrocarbyl groups of 4 to 10 carbon atoms;

(b) ether alcohol of the formula:

R"—(O—(CH$_2$)$_x$)$_n$—OH wherein R" is an aliphatic hydrocarbyl group of 1 to 20 carbon atoms, x is 2 to 3, and n is 1 to 10; and (d) phenolic monoether selected from the group consisting of methoxybenzene and ethoxybenzene ether.

8. A process according to claim 7, wherein the organic compound is said ether alcohol of group (b) wherein R" is alkyl of 2 to 6 carbon atoms.

9. A process according to claim 7 in which said organic compound is said phenolic monoether of group (d).

10. A composition comprising a concentrate of 50 to 90 wt. % of oil soluble alkarylsulphonic acid having a mean molecular weight of about 350 to about 600, and a hydrocarbon oil as diluent; and in the range of about 0.05 up to 5 wt. %, based on the weight of said concentrate, of an organic compound selected from the group consisting of:

(b) ether alcohol of the formula:

R"—(O—(CH$_2$)$_x$)$_n$—OH wherein R" is an aliphatic hydrocarbyl group of 1 to 20 carbon atoms, x is 2 to 3, and n is 1 to 10; and (d) phenolic monoethers selected from the group consisting of methoxybenzene, ethoxybenzene, diphenyl ether and dibenzyl ether.

11. A composition according to claim 10, wherein said organic compound is the ether alcohol of group (b) where R" is alkyl of 2 to 6 carbon atoms.

12. A composition according to claim 10, in which said organic compound is a phenolic monoether of group (d).

* * * * *